United States Patent
Dillon

(10) Patent No.: US 10,463,601 B1
(45) Date of Patent: Nov. 5, 2019

(54) TOPICAL COSMETIC COMPOSITION

(71) Applicant: Lorita Dillon, Veedersburg, IN (US)

(72) Inventor: Lorita Dillon, Veedersburg, IN (US)

(73) Assignee: Lorita Dillon, Veedersburg, IN (US)

( * ) Notice: Subject to any disclaimer, the term of this patent is extended or adjusted under 35 U.S.C. 154(b) by 207 days.

(21) Appl. No.: 15/185,288

(22) Filed: Jun. 17, 2016

(51) Int. Cl.
| | |
|---|---|
| *A61K 36/61* | (2006.01) |
| *A61K 8/92* | (2006.01) |
| *A61K 8/49* | (2006.01) |
| *A61Q 19/08* | (2006.01) |

(52) U.S. Cl.
CPC .............. *A61K 8/922* (2013.01); *A61K 8/498* (2013.01); *A61K 8/4973* (2013.01); *A61K 8/92* (2013.01); *A61Q 19/08* (2013.01)

(58) Field of Classification Search
None
See application file for complete search history.

(56) References Cited

U.S. PATENT DOCUMENTS

| | | |
|---|---|---|
| 5,885,596 A | 3/1999 | Parab |
| 5,997,889 A | 12/1999 | Durr et al. |
| 2005/0186171 A1 | 8/2005 | Winick |
| 2016/0213757 A1* | 7/2016 | Edelson ............... A61K 8/06 |
| 2017/0087199 A1* | 3/2017 | Patron ................. A61K 36/81 |
| 2017/0333346 A1* | 11/2017 | Burnam ................ A61K 9/10 |
| 2018/0193244 A1* | 7/2018 | Hood .................... A61K 8/49 |

FOREIGN PATENT DOCUMENTS

| | | |
|---|---|---|
| EP | 2253304 A2 | 2/2009 |
| EP | 2253304 A2 * | 11/2010 |

* cited by examiner

*Primary Examiner* — Ralph J Gitomer

(57) ABSTRACT

A method of preparation of a topical composition for wrinkle or lines reduction when applied to face and neck is disclosed. The method of preparation of topical composition uses the following ingredients: Purified Water, Vitamin C tablets (natural 1000 mg), Vitamin E capsules (natural 1000 mg), emulsified wax, Essential Oils (Argan, Johoba, Coconut, & Lavender, Tea Tree Oil), & Cornstarch. The method of preparation of topical composition uses the following amounts of each ingredient: 2¾ cup Purified Water 12 Vitamin C Tablets; 15 Vitamin E Capsules; 1 Tablespoon plus ¾ teaspoon Emulsified Wax granules; 1 Tablespoon Johoba Oil; 2 teaspoons Argan Oil; 2 teaspoons Coconut Oil; 4 Tablespoons Cornstarch; ½ teaspoon Lavender Oil, 0.03 ounces Tea Tree Oil or 1 cubic centimeter (cc) syringe. The topical composition can be used with minor changes for both genders with equal effectiveness.

1 Claim, No Drawings

TOPICAL COSMETIC COMPOSITION

FIELD OF THE INVENTION

The present invention relates to a method for reducing fine lines and/or wrinkles on the skin. More particularly, to a method for providing topical compositions for the effacement of facial fine lines and/or wrinkles, as well as other beneficial effects like adding firmness and adding softness to skin touch.

BACKGROUND OF THE INVENTION

The prior art is replete with compositions for mitigating dermatological conditions of the skin which frequently relate to the natural process of aging. Other factors, such as exposure to the sun or the resulting ultraviolet radiation therefrom, improper care and/or diet, stress, nutritional deficiencies, and genetic propensities also contribute to the development of adverse skin conditions, such as fine lines, wrinkles, especially of the facial skin, age spots, keratoses, dry skin, lack of skin tautness and suppleness, and depigmentation. Many of the compositions described for topical treatment of the skin include components which have adverse side effects to the user, such as drying, burning, stinging, scaling and itching, irritation to the skin, and induction of photosensitivity. Therefore, methods and compositions commonly used for reducing fine lines and/or wrinkles contain acids, particularly, alpha (α)-hydroxy acids, such as glycolic acid, lactic acid, tartaric acid and citric acid, and salts thereof, or they contain tretinoin, also known as all-trans retinoic acid or retinol (Vitamin A), or ascorbic acid (Vitamin C), all of which can induce the above-mentioned disadvantageous effects, often due to a lowering of the pH of the skin, among other factors. With particular regard to topical compositions containing tretinoin, medical reports have documented a number of other adverse skin reactions typically associated with their use, namely, burning, tingling, stinging, dryness, peeling, erythema, itching, skin dermatitis, localized swelling and sun sensitivity.

Various prior art patents have disclosed solutions to this problem, for example, U.S. Pat. Nos. 6,551,607 and 6,521,241 relate to a method of sequestering skin irritants with a skin irritant sequestering composition comprising a substrate, a hydrophilic skin irritant sequestering agent and a hydrophobic skin irritant sequestering agent. U.S. Pat. No. 6,517,848 relates to a method for sequestration of skin irritants with absorbent article compositions. The composition comprises an absorbent article having disposed thereon a skin irritant sequestering effective amount of an unmodified particulate skin irritant sequestering agent and a lipophilic skin health benefit agent. A lipophilic skin health benefit agent can be stearic acid, iso-parrafin, petrolatum, and a combination thereof. U.S. Pat. No. 6,534,074 relates to a superior skin barrier enhancing body facing material, such as a body sideliner on an absorbent article and can be made by applying on the outer surface of the body facing material, a lipid-enriched hydrophobic composition comprising a natural fat or oil, a sterol, or sterol derivative, an emulsifying surfactant, a humectant, an emollient, a wax, and a viscosity enhancer, and thereafter re-solidifying the composition to form a distribution of solid composition on the outer surface of the body facing material.

U.S. Pat. No. 6,485,733 relates to an absorbent article composition for sequestering skin irritants. The article has disposed thereon a skin irritant sequestering effective amount of an unmodified particulate skin irritant sequestering agent and a lipophilic skin health benefit agent. An unmodified particulate skin irritant sequestering agent can be a clay, such as bentonite or laponite unmodified by organic amphiphilic compounds. A lipophilic skin health benefit agent can be stearic acid, isoparrafin, petrolatum, and a combination thereof. U.S. Pat. No. 6,342,208 relates to an oil-water emulsion for application on a skin surface. The emulsion comprises an oily phase and an aqueous phase. The oily phase comprises a first lipid of vegetable or animal origin. The emulsion is stabilized by containing at least one surfactant/emulsifier. U.S. Pat. No. 6,312,714 relates to a cosmetic composition for rejuvenating the appearance of skin with reduced or minimal potential for skin irritation, in the form of a lotion, creme, solution or gel, or applied onto a carrier, and includes about 0.5 to 50 wt. % in an aqueous, alcoholic or aqueous-alcoholic solution of a solvent-free, high molecular weight terpolymer of methyl vinyl ethermaleic anhydride-isobutylene, said composition having a pH of 1.5 to 5.

U.S. Pat. No. 6,287,581 relates to a superior skin barrier enhancing body facing material, such as a body side liner on an absorbent article and can be made by applying on the outer surface of the body facing material, a lipid-enriched hydrophobic composition comprising a natural fat or oil, a sterol or sterol derivative, an emulsifying surfactant, a humectant, an emollient, a wax, and a viscosity enhancer, and thereafter resolidifying the composition to form a distribution of solid composition on the outer surface of the body facing material. U.S. Pat. No. 5,985,809 relates to a personal cleansing composition comprising: (a) from about 1% to about 30% by weight of a dispersed oil phase comprising at least one nonocculsive liquid polyol fatty acid polyester containing at least four fatty acid ester groups wherein the polyol moiety is selected from sugars and sugar alcohols containing from about 4 to about 8 hydroxyl groups, and wherein each carboxylic acid moiety has from about 8 to about 22 carbon atoms and wherein the liquid polyol fatty acid polyester has a complete melting point of less than about 30° C.; and (b) from about 5% to about 30% by weight of water-soluble surfactant selected from anionic, nonionic, zwitteri onic and amphoteric surfactants and mixtures thereof.

Therefore there is a need to provide a method of making topical compositions for skin wrinkles reduction that is easy to make and cost effective giving all the benefits of expensive skin compositions without producing irritant side effects to the user. Additionally, it is desirable that such a composition can be manufactured by simple process steps that results in a softer to touch and firmer skin for the user.

SUMMARY

A method of preparation of a topical composition for wrinkle or lines reduction when applied to face and neck is disclosed. The method of preparation of topical composition uses the following ingredients: Purified Water, Vitamin C tablets (natural 1000 mg), Vitamin E capsules (natural 1000 mg), emulsified wax, Essential Oils (Argan, Johoba, Coconut, & Lavender, Tea Tree Oil), & Cornstarch. The method of preparation of topical composition uses the following amounts of each ingredient: 2¾ cup Purified Water 12 Vitamin C Tablets; 15 Vitamin E Capsules; 1 Tablespoon plus ¾ teaspoon Emulsified Wax granules; 1 Tablespoon Johoba Oil; 2 teaspoons Argan Oil; 2 teaspoons Coconut Oil; 4 Tablespoon Cornstarch; ½ teaspoon Lavender Oil, 0.03 ounces Tea Tree Oil or 1 cubic centimeter (cc) syringe. The topical composition can be used with minor changes for both genders with equal effectiveness.

It is an object of the present invention to provide a method of preparation of topical composition targeted at causing significant reduction in facial lines and wrinkles.

It is further an object of the present invention to provide a method of preparation of topical composition that may be used with minor changes for both genders with equal effectiveness.

It is yet another object of the present invention to provide a method of preparation of topical composition that is uses natural ingredients that effectively diminishes wrinkles on the face and neck.

There has thus been outlined, rather broadly, the more important features of the invention in order that the detailed description thereof that follows may be better understood and in order that the present contribution to the art may be better appreciated.

DETAILED DESCRIPTION OF THE INVENTION

The present invention provides an improved method of manufacturing a topical composition. The purpose of the invention is to provide a user friendly process which is based on natural products with essential oils. Referring to the invention now in more detail, the invention is directed to wrinkle or lines reduction using a topical composition, when applied to the user's face and neck area. The method of preparation of topical composition as provided in the current invention uses the ingredients: Purified Water, Vitamin C tablets (natural 1000 mg), Vitamin E capsules (natural 1000 mg), emulsified wax, Essential Oils (Argan, Johoba, Coconut, & Lavender, Tea Tree Oil), & Cornstarch. The recipe used: 2¾ cup Purified Water 12 Vitamin C Tablets; 15 Vitamin E Capsules; 1 Tablespoon plus ¾ teaspoon Emulsified Wax granules; 1 Tablespoon Johoba Oil; 2 teaspoons Argan Oil; 2 teaspoons Coconut Oil; 4 Tablespoon Cornstarch; ½ teaspoon Lavender Oil, Tea Tree Oil. The topical composition can be used with minor changes for both genders with equal effectiveness. The topical composition is susceptible to a low cost of manufacture with regard to both materials and labor and can be even manufactured in one's home kitchen using the tools and method as described herein.

Ingredients: Facial Cream
Purified Water, Vitamin C tablets (natural 1000 mg), Vitamin E capsules (natural 1000 mg), emulsified wax, Essential Oils (Argan, Johoba, Coconut, Tea Tree Oil, Lavender), & Cornstarch.

Amount of Each Ingredient Needed:
2¾ cup Purified Water
12 Vitamin C Tablets
15 Vitamin E Capsules
1 Tablespoon plus ¾ teaspoon of Emulsified Wax granules
1 Tablespoon Johoba Oil
2 teaspoons Argan Oil
2 teaspoons Coconut Oil
4 Tablespoon Cornstarch
½ teaspoon Lavender Oil
0.03 ounces Tea Tree Oil or 1 cubic centimeter (cc) syringe.
Method of Preparation:
The method for the preparation of the topical composition involves the following steps:

1. Using a double boiler place 2 inches of water in the lower part of the double boiler and place over medium heat. Thereafter, place the top boiler inside of the lower double boiler pan.
2. measure the emulsified wax to melt.
3. lower the heat after the wax has melted (roughly it takes 5 minutes to melt) so the wax will keep liquid consistency.
4. grind all the Vitamin C tablets into small pieces or powder and set pieces/powder aside
5. boil two (2) cups of water into a medium sauce pan at when the water is boiling pour the Vitamin C pieces/powder into sauce pan and stir (approximately 2-3 minutes) or until the tablets have completely dissolved. Turn down heat to low.
6. While stirring the mixture in the sauce pan, gently pour the emulsified wax into the medium sauce pan and continue to stir for a 1 minute. This binds the water and the oils together when needed. Keep heat low.
7. Pour ½ cup of water into small sauce pan and place on the burner (not turned on at this time). Place each of the Vitamin E capsules on a cutting board and puncture a hole big enough to squeeze out most of the liquid out of the capsules in the small sauce pan then drop the capsule in the water also. This process makes sure that all the Vitamin E will thoroughly dissolve when heat is added. Take a metal spoon to stir and turn on burner to medium heat, stirring constantly. This mixture will turn bright white and will have a tendency to stick. Turn off burner under small sauce pan.
8. Pour the small sauce pan of Vitamin E solution in the medium sauce pan, this should already be at a low boil, stirring constantly (use spatula to get all Vitamin E mixture out of small sauce pan completely) until the mixture is well blended approximately 1 minute. Keep heat on low.
9. Measure Cornstarch in a small bowl and add ¼ cup to ⅓ cup of water. Use fork to smooth out the mixture making sure that no lumps are left. Turn the medium sauce pan heat up to medium. This must be a rolling boil (bubbly) before adding the Cornstarch mixture.
10. After the sauce pan begins to boil pour the Cornstarch mixture in and stir quickly but constantly for 1-2 minutes or until it has a thickened consistency. Turn off heat.
11. Remove medium sauce pan from heat and pour into a medium mixing bowl to cool. The mixture should be approximately 80 degrees Fahrenheit. Use a small mixer periodically to help cool and keep the mixture smooth.
12. After mixture has cooled add the Essential Oils (Argan, Johoba, Coconut, Tea tree oil and Lavender) one at a time using the mixer to blend all oils well. Continue to let the mixture cool completely before filling storage containers.
13. Fill 4 ounce or larger storage containers with a spoon and seal with a tight lid in dark/cool area.
Caution: It should be understood that this product is to be used externally only. It is not to be ingested by mouth. Keep out of eyes if contacted wash out thoroughly with water.

Hereinafter, example embodiments will be described in detail with reference to the following examples. However, these examples are not intended to limit the purpose and scope of example embodiments.

Example 1

Facial Cleanser for Ladies:
Ingredients:
2¾ cups Purified Water will achieve the same purpose, may be substituted for the specific embodiment shown.

Other allocations of functionality are envisioned and may fall within the scope of the inventive subject matter. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

What is claimed is:

1. A topical emulsified composition for reducing fine lines and wrinkles on skin, the composition consisting essentially of:

| | |
|---|---|
| Purified water | 2.75 cups, |
| Vitamin C | 12 1 gram tablets, |
| Vitamin E | 15 1 gram capsules, |
| Emulsified wax granules | 1 tablespoon plus 0.75 teaspoon, |
| Jojoba oil | 1 tablespoon, |
| Argan oil | 2 teaspoons, |
| Coconut oil | 2 teaspoons, |
| Cornstarch | 4 tablespoons, |
| Lavender oil | 0.5 teaspoons, and |
| Tea Tree oil | 1 cubic centimeter. |

\* \* \* \* \*